United States Patent [19]
O'Brien et al.

[11] Patent Number: 5,808,093
[45] Date of Patent: Sep. 15, 1998

[54] L-TARTARIC ACID SALT OF A (1R) DIASTEREOMER OF A 2-AZADIHYDROXYBICYCLO[2.2.1]HEPTANE COMPOUND AND THE PREPARATION OF 2-AZABICYCLO[2.2.1]HEPTANE COMPOUNDS

[75] Inventors: Michael O'Brien, Berwyn, Pa.; Patrick Leon, Tassin la Demi Lune; Denis Largeau, Taluyers, both of France; Ching Tsuei, Lansdale, Pa.; Thierry Durand, Challes Les Eaux, France

[73] Assignee: Rhone-Poulenc Rorer S.A., Antony, France

[21] Appl. No.: 873,285

[22] Filed: Jun. 10, 1997

Related U.S. Application Data

[60] Division of Ser. No. 732,024, Oct. 16, 1996, Pat. No. 5,684,159, which is a continuation-in-part of Ser. No. 655,395, May 30, 1996, Pat. No. 5,670,649, which is a continuation-in-part of Ser. No. 476,156, Jun. 7, 1995, Pat. No. 5,631,383.

[30] Foreign Application Priority Data

May 30, 1995 [FR] France .................. FR95-06353

[51] Int. Cl.$^6$ ................................. C07D 209/52
[52] U.S. Cl. ............................................. 548/452
[58] Field of Search ............................... 548/452

[56] References Cited

U.S. PATENT DOCUMENTS

| | | | |
|---|---|---|---|
| 5,137,908 | 8/1992 | Fourie et al. | 514/410 |
| 5,284,769 | 2/1994 | Evans et al. | 435/280 |
| 5,700,895 | 12/1997 | Kanda et al. | 526/348 |

*Primary Examiner*—Joseph McKane
*Attorney, Agent, or Firm*—Raymond S. Parker, III; Martin F. Savitzky

[57] ABSTRACT

A compound of formula

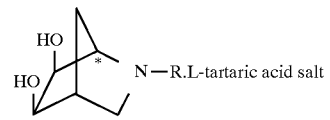

wherein
R is a group of formula

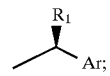

$R_1$ is alkyl; and
Ar is optionally substituted aryl.

1 Claim, No Drawings

L-TARTARIC ACID SALT OF A (1R) DIASTEREOMER OF A 2-AZADIHYDROXYBICYCLO[2.2.1]HEPTANE COMPOUND AND THE PREPARATION OF 2-AZABICYCLO[2.2.1]HEPTANE COMPOUNDS

This application is a divisional of U.S. patent application Ser. No. 08/732,024, filed Oct. 16, 1996, now U.S. Pat. No. 5,684,159 which in turn is a continuation-in-part of U.S. patent application Ser. No. 08/655,395, filed May 30, 1996, now U.S. Pat. No. 5,670,649 which in turn is a continuation-in-part of U.S. patent application Ser. No. 08/476,156, filed Jun. 7, 1995, now U.S. Pat. No. 5,631,383, issued May 20, 1997.

FIELD OF THE INVENTION

The present invention is directed to a method for preparing a 2-azadihydroxybicyclo[2.2.1]heptane compound. The invention is also directed to an L-tartaric acid salt of the (1R) diastereomer of the 2-azadihydroxybicyclo[2.2.1]heptane compound and its preparation. In addition, the invention is directed to a method for bis O-protection of the (1R) diastereomer of the 2-azadihydroxybicyclo[2.2.1]heptane compound and a method for oxidizing derivatives of the (1R) diastereomer of the 2-azadihydroxybicyclo[2.2.1]heptane compound to a corresponding lactam compound.

U.S. Pat. No. 5,284,769 discloses that a lactam compound, which encompasses a lactam compound prepared according to the invention, as being a useful synthon for preparing pharmaceutically active agents. J. Chen et al., Tet. Lett., 30 5543 (1989) disclose a lactam compound, which encompasses a lactam compound prepared according to the invention, as being used in preparing a compound that is active as an adenosine agonist.

Reported Developments

C. K. -F. Chui, Syn. Comm., 26(3), 577 (1996) discloses resolving a diastereomeric mixture of bicycloheptenamine compounds of formulae (i) and (ii)

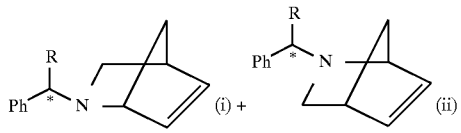

using L-dibenzoyl tartaric acid, i.e., by fractional crystallization. The Chui reference does not disclose means for resolving bishydroxylated products of the diastereomeric mixture.

S. J. C. Taylor et al., Tetrahedron: Asymmetry, 4(6), 1117 (1993) disclose the enzymatic resolution of a lactam of formula (iii)

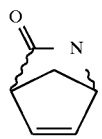

to yield the enantiomers of formulae (iv) and (v)

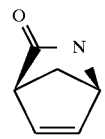

and

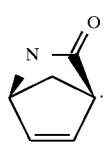

S. J. C. Taylor et al. do not disclose any means for resolving bishydroxylated products of the lactam (iii).

U.S. Pat. No. 5,284,769 discloses the enzymatic resolution of a lactam of formula (vi)

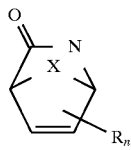

to yield the enantiomers of the lactam. U.S. Pat. No. 5,284,769 does not disclose any means for resolving bishydroxylated products of the lactam (vi).

SUMMARY OF THE INVENTION

A method according to the invention is directed to the preparation of a 2-azadihydroxybicyclo[2.2.1]heptane compound of formula

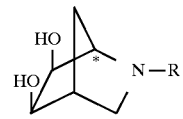

or

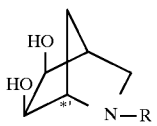

wherein * represents an R chirality, *' represents an S chirality, R is hydrogen or, respectively, a group of formula

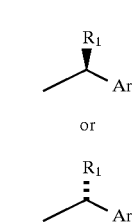

wherein $R_1$ is alkyl and Ar is optionally substituted aryl, comprising bishydroxylating a bicyclo[2.2.1]heptene compound of formula

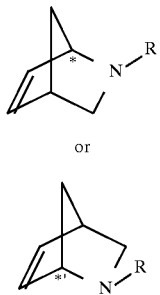

wherein *, *' and R are as previously defined, in the presence of about 0.1 mol % to about 5 mol % of a metal osmate compound or about 0.06 mol % to about 0.07 mol % osmium tetroxide, and an oxidizing agent capable of regenerating osmium tetroxide.

The invention is also directed to the treatment of the (1R) diastereomer of the 2-azadihydroxybicyclo[2.2.1]heptane compound (I) wherein R is a group of formula II with L-tartaric acid, and the L-tartaric acid salt product thereof. Furthermore, the invention is directed to using the (1R) diastereomer of the 2-azadihydroxybicyclo[2.2.1]heptane compound or salt thereof in an acid facilitated acetalizing or ketalizing reaction that results in the protection of the dihydroxy moieties thereof in isopropanol. In addition, the invention is directed to oxidizing a bis O-protected derivative of the (1R) diastereomer of the 2-azadihydroxybicyclo-[2.2.1]heptane compound to a corresponding lactam compound in the presence of about 0.01 mol % to about 1 mol % of $RuO_2$ or hydrate thereof with about 3 equivalents of an oxidant to form the lactam compound in an enantiomeric excess ("ee") of greater than or equal to about 95%.

DETAILED DESCRIPTION OF THE INVENTION

As used above, and throughout the description of the invention, the following terms, unless otherwise indicated, shall be understood to have the following meanings.

"Alkyl" means an aliphatic hydrocarbon group which may be straight or branched having 1 to about 4 carbon atoms. Exemplary alkyl groups include methyl, ethyl, i-propyl and t-butyl.

"Optionally substituted methylene" means —$CH_2$— or that moiety wherein the hydrogen atoms are replaced individually by one or two groups, which may be identical or different, selected from alkyl or phenyl, or replaced concomitantly to form, together the carbon atom of the methylene, cycloalkyl.

"Aryl" means optionally substituted phenyl or optionally substituted α- or β-naphthyl. A substituted aryl is substituted by one or more aryl group substituents, which may be identical or different, which include halo, alkyl, alkoxy, and nitro.

"Alkoxy" means an alkyl—O— group wherein the alkyl group is as previously described. Exemplary alkoxy groups include methoxy, ethoxy, i-propoxy and t-butoxy.

"Cycloalkyl" means an aliphatic cyclic ring of about 5 to about 6 carbon atoms. An exemplary cycloalkyl group is cyclohexyl.

"Acyl" means an alkyl—CO— group wherein the alkyl group is as previously described. Exemplary acyl groups include acetyl and propanoyl.

"Aroyl" means an aryl—CO— group wherein the aryl group is as previously described. An exemplary aroyl group is benzoyl.

"Halo" means fluoro, chloro, bromo or iodo. Preferred are fluoro and chloro.

"Oxidizing agent capable of regenerating osmium tetroxide" means an oxidant that will oxidize the osmium of the metal osmate ($Os^{+6}$) to osmium tetroxide ($Os^{+8}$) or reoxidizes the osmium tetroxide reduced in effecting the bishydroxylation to osmium tetroxide ($Os^{+8}$). Examples of oxidizing agents capable of regenerating osmium tetroxide include N-methylmorpholine oxide or triethylamine oxide and potassium ferricyanide ($K_3FeCN_6$), preferred is N-methylmorpholine oxide.

"Metal osmate" means a salt compound formed from $M^{n+}$, a metal cation wherein n is 1 or 2, and an osmium oxide anion complex $[OsO_4]^{-2}$, or hydrates thereof. Preferable metal osmates are alkali or alkaline earth osmates, including sodium, potassium, rubidium, cesium, calcium and barium osmates, more preferable is $K_2OsO_4 \cdot 2H_2O$. Examples of methods useful for preparing metal osmates are described by B. N. Ivanov-Emin et al., Zh. Neorg. Khim. 31(5) 1238 (1986), H. C. Jewiss, J. C. S. Dalton Trans. 199 (1985), B. N. Ivanov-Emin et al., Zh. Neorg. Khim. 29(4) 1241 (1984), B. N. Ivanov-Emin et al., Zh. Neorg. Khim. 28(5) 1246 (1983).

"Salt thereof" means the compound with a basic moiety neutralized by an acid to form the corresponding acid addition salt. Acids which can be used to prepare the acid addition salts include preferably those which produce, when combined with the free base, pharmaceutically acceptable salts, that is, salts whose anions are non-toxic to a patient, and so that subsequent use of the acid addition salt does not proscribe the salt from subsequent chemical reactivity. The acid addition salt is useful for example as a source for the regeneration of the base compound therein by treatment with a base such as alkali, for purposes of purification and/or identification, or for interconversion to another acid addition salt form by an ion exchange procedures. Examples of acid addition salts include those encompassing the following acids: mineral acids such as hydrobromic, hydrochloric acid, sulfuric acid, phosphoric acid and sulfamic acid; and organic acids such as acetic acid, citric acid, lactic acid, tartaric acid, dibenzoyltartaric, malonic acid, succinic, 2,3-dimethoxysuccinic, methanesufonic acid, ethanesulfonic acid, benzenesulfonic acid, p-toluenesulfonic acid, cyclohexylsulfamic acid, quinic acid, and the like.

Preferred Embodiments

A special embodiment for the bishydroxylation method according to the invention, is that wherein R is a group of formula II or II'.

A preferred embodiment for the bishydroxylation method according to the invention, is that wherein $R_1$ is methyl or ethyl, and Ar is optionally substituted phenyl, which when substituted is substituted by one or more methyl or methoxy.

A more preferred embodiment for the bishydroxylation method according to the invention, is that wherein $R_1$ is methyl, and Ar is phenyl.

A preferred embodiment for effecting the bishydroxylation uses the osmium tetroxide at about 0.06 mol % to about 0.07 mol %, more preferably at about 0.06 mol %.

Another preferred embodiment for effecting the bishydroxylation uses the metal osmate at about 0.1 mol % to about 5 mol %, more preferably at about 0.2 to about 0.5 mol %.

Yet, another preferred embodiment for effecting the bishydroxylation uses an alkali or alkaline earth osmate as the metal osmate, more preferably $K_2OsO_4 \cdot 2H_2O$.

A special embodiment for preparing the L-tartaric acid salt of the (1R) diastereomer of the 2-azadihydroxybicyclo[2.2.1]heptane compound, i.e.,

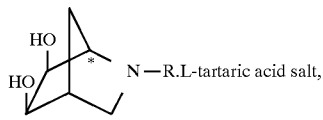

according to the invention, is that wherein R is a group of formula II.

A preferred embodiment for preparing the L-tartaric acid salt of the (1R) diastereomer of the 2-azadihydroxybicyclo[2.2.1]heptane compound according to the invention, is that wherein $R_1$ is methyl and Ar is phenyl.

Another special embodiment according to the invention is for preparing the L-tartaric acid salt of the (1R) diastereomer of the 2-azadihydroxybicyclo[2.2.1]heptane compound in a substantially enantiomerically purified state in the presence of a (1S) diastereomer of the 2-azadihydroxybicyclo[2.2.1]heptane compound.

A preferred embodiment for preparing the L-tartaric acid salt of the (1R) diastereomer of the 2-azadihydroxybicyclo[2.2.1]heptane compound according to the invention, is that wherein the preparation occurs in an aqueous-organic solvent mixture.

A more preferred embodiment for preparing the L-tartaric acid salt of the (1R) diastereomer of the 2-azadihydroxybicyclo[2.2.1]heptane compound according to the invention, is that wherein the organic solvent is isopropanol (IPA).

An even more preferred embodiment for preparing the L-tartaric acid salt of the (1R) diastereomer of the 2-azadihydroxybicyclo[2.2.1]heptane compound according to the invention, is that wherein the preparation occurs in an aqueous-IPA solvent mixture having a volume ratio of about 30:70 to about 15:85, further preferably of about 25:75.

A special embodiment for the acid facilitated acetalizing or ketalizing reaction method according to the invention, is directed to a method for preparing a compound of formula IV

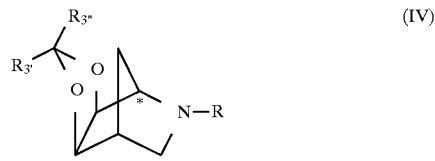

wherein R is as defined herein, $R_{3'}$ and $R_{3''}$ are hydrogen, alkyl or phenyl, or $R_{3'}$ and $R_{3''}$ taken together with the carbon atom to which they are attached form a cycloalkyl, comprising acid facilitated acetalizing or ketalizing of a compound of formula V

wherein $R_{4'}$ and $R_{4''}$ are alkoxy, or taken together with the carbon atom to which they are attached form carbonyl, with the (1R) diastereomer of the 2-azadihydroxybicyclo[2.2.1]heptane as described herein or salt thereof in IPA.

A preferred embodiment for the acid facilitated acetalizing or ketalizing reaction is that wherein $R_{4'}$ and $R_{4''}$ are methoxy and $R_{3'}$ and $R_{3''}$ are methyl.

Another preferred embodiment for the acid facilitated acetalizing or ketalizing reaction is that wherein the acid facilitation is effected using trifluoroacetic acid (TFA).

Yet another preferred embodiment for the acid facilitated acetalizing or ketalizing reaction is that wherein R is a group of formula II.

A more preferred embodiment for the acid facilitated acetalizing or ketalizing reaction is that wherein $R_1$ is methyl and Ar is phenyl.

Still another preferred embodiment for the acid facilitated acetalizing or ketalizing reaction is that wherein the (1R) diastereomer of the 2-azadihydroxybicyclo[2.2.1]heptane compound is in the form of an L-tartaric acid salt thereof.

A special embodiment for the lactam preparative method according to the invention, is directed to a method for preparing a lactam compound of formula VI

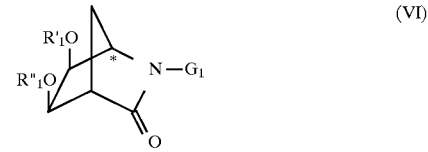

wherein $R'_1$ and $R''_1$ independently are acyl or aroyl, or taken together form an optionally substituted methylene, and $G_1$ is hydrogen or an amino protecting group, comprising oxidizing a bis O-protected (1R) diastereomer of the 2-azadihydroxybicyclo[2.2.1]heptane compound of formula VII

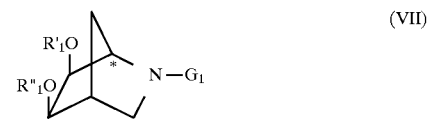

in the presence of about 0.1 mol % to about 1 mol % of $RuO_2$ or hydrate thereof with about 3 equivalents of an oxidant to form the lactam compound with an ee of greater than or equal to about 95%.

A preferred embodiment for the lactam preparative method is that wherein the $RuO_2$ is present at about 0.5 mol %.

Another preferred embodiment for the lactam preparative method is that wherein the lactam compound is formed with an ee of greater than or equal to about 99%.

General parameters for the preparative methods are those described heretofore and below.

In general, the bishydroxylation is carried out under the conditions described by V. VanRheenen et al., Tetrahedron Letters, Vol. 23, 1973–1976 (1976). The oxidant must effect the bishydroxylation in the exo form. More particularly, the oxidation can be carried out by means of potassium permanganate or osmium tetroxide or a metal osmate and working in the presence of N-methylmorpholine oxide or triethylamine oxide or potassium ferricyanide ($K_3FeCN_6$).

According to the invention the osmium tetroxide is employed in a catalytic amount which results in a more effective control of osmium residues in the product. The reaction with the osmium may occur with as little as about 0.06 mol % to about 0.1 mol % which takes respectively from about 21 to about 5 hours. The reaction preferably takes place with about 0.06 mol % osmium tetroxide. The oxidation may take place in an aqueous-organic solvent medium such as water-t-butanol or water-acetone, more preferably water-acetone. An ether solvent such as t-butyl methyl ether or di-i-propyl ether may additionally be present when the oxidation is carried out in an water-acetone solvent medium. A preferred range of volume amounts of ether:acetone:water solvent mixture is about 1.9:16.7:1 of ether/acetone to about 11.1:7.4:1; more preferred is 11.1:16.7:1 to 16.7:16.7:1.

The bishydroxylation can also be effected in the same manner on a mixture of the diastereomers (I) and (I'), i.e., without them having to be separated before effecting the bishydroxylation.

The (1R) diastereomer of formula I, wherein R is a group of formula II, can be isolated as salts of optically-active organic acids, and more especially from a mixture of diastereomeric compounds of formulae I and I' by diastereoselective crystallization using such optically-active organic acids. One useful optically-active organic acid is L-dimethoxysuccinic acid. The salt formation using L-dimethoxysuccinic acid is carried out in an appropriate organic solvent such as a ketone or an aliphatic alcohol, particularly advantageous is IPA. According to the invention, L-tartaric acid is another useful optically-active organic acid. The salt formation using L-tartaric acid acid is carried out in a solvent such as an aqueous-organic solvent mixture wherein the organic solvent such as an aliphatic alcohol such as IPA. The use of L-tartaric acid results in improved yields and enantiomeric purity of the desired diastereomer (I).

The dihydroxy moieties of a compound of formula I, wherein R is hydrogen or a group of formula II, can be protected in the form of an ester or acetal/ketal to yield a product of formula VIII

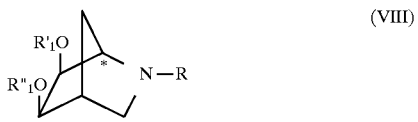

(VIII)

wherein R is hydrogen or a group of formula II, and $R'_1$ and $R''_1$ are as defined before.

In general, the protection of the hydroxy groups is achieved under either esterification or acetalization/ketalization conditions. For example, esterification takes place by reacting an acyl containing group such as acetic acid or propionic acid in the presence of p-toluenesulfonic acid in an organic solvent such as an aromatic hydrocarbon, for example, benzene or toluene, by separating the water gradually, for example azeotropically, as it is formed. For example, acetalization/ketalization is effected by reacting an aldehyde or a ketone, possibly in the form of ketal, in the presence of an acid such as TFA in an organic solvent such as an aliphatic alcohol, for example, IPA, aromatic hydrocarbon, for example, benzene or toluene, or ether, for example, t-butyl methyl ether or di-i-propyl ether, at about 50° C. to about the boiling point of the reaction mixture. When an ether solvent is used acetic may acid may also be present which results in formation of a salt of the compound of formula IV that is extractable in water. A preferred ketalization medium, according to the invention, comprises the use of 2,2-dimethoxypropane, TFA and IPA to give improved yield and enantiomeric excess of the product. The reaction takes place at about 70° C.

The product of formula VIII wherein R is a group of formula II can be transformed into a product of formula VIII wherein R is hydrogen by hydrogenolysis. In general, the hydrogenolysis is carried out by means of hydrogen, which is optionally pressurized, in the presence of a catalyst such as palladium on charcoal in an organic solvent such as an alcohol, for example, methanol, ethanol or IPA, at about 0° C. to about 50° C. A product of formula VIII wherein R is hydrogen is also be formed employing the same hydrogenolysis reagents and conditions on the salt of the compound of formula IV wherein R is a group of formula II.

The product of formula VIII wherein R is hydrogen can be transformed into a product of formula IX

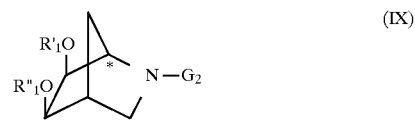

(IX)

wherein $R'_1$ and $R''_1$ are defined as before and $G_2$ is an amino protecting group, by the selective introduction of an appropriate protecting group.

The protecting groups are selected from those which can later be removed selectively. These protecting groups include the following, which are particularly well suited: t-butoxycarbonyl, chloroacetyl, methoxymethyl, trichloro-2,2,2-ethoxycarbonyl, t-butyl, benzyl, p-nitrobenzyl, p-methoxybenzyl, diphenylmethyl, trialkylsilyl, allyloxycarbonyl, and benzyloxycarbonyl groups, wherein the phenyl ring is optionally substituted by halo, alkyl or alkoxy. Among the protecting groups which are particularly well suited, one can mention those described by T. W. Greene and P. G. M. Wuis, "Protecting Groups in Organic Synthesis," Chapter 7, 2nd edition, John Wiley & Sons (1991). The t-butoxycarbonyl group is of particular interest.

The product of formula IX wherein $G_2$ is t-butoxycarbonyl can be obtained directly from a product of formula VIII wherein R is the group of formula II by simultaneous hydrogenolysis and t-butoxycarbonylation.

For example, the reaction is carried out by simultaneously reacting hydrogen in the presence of a catalyst such as palladium and charcoal and di-t-butyl dicarbonate with a product of formula VIII wherein R is a group of formula II in an organic solvent such as an alcohol, for example, methanol, ethanol or IPA, about 0° C. to about 50° C. This reaction is particularly useful where $R'_1$ and $R''_1$ taken together form an optionally substituted methylene.

Alternatively, the product of formula IX wherein $G_2$ is t-butoxycarbonyl can be obtained in two steps from a product of formula VIII wherein R is the group of formula II by first effecting the hydrogenolytic removal of the group of formula II to yield the corresponding product wherein R is hydrogen, and second effecting the t-butoxycarbonylation of that product. The hydrogenolytic removal is effected as previously described, and the t-butoxycarbonylation is effected in water under alkaline conditions using $(Boc)_2O$.

The product of formula IX is then oxidized into a product of formula X

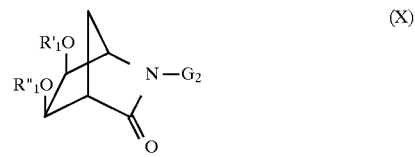

(X)

wherein $R'_1$, $R''_1$ and $G_2$ are defined as above.

In general, the oxidation is conducted by means of ruthenium oxide ($RuO_4$), which can be optionally generated in situ from a precursor such as $RuO_2$ or $RuCl_3$ in the presence of an oxidant selected from a periodate such as sodium periodate, a hypohalite such as hypochlorite or sodium hypobromite or a bromate such as sodium bromate or an organic tertiary amine oxide such as N-methylmorpholine oxide or triethylamine oxide. The reaction takes place in a solvent such as water or a homogeneous or heterogeneous aqueous-organic medium, such as a water-EtOAc mixture.

The oxidation can also be conducted using sodium hypochlorite alone or using potassium permanganate or sodium tungstate in the presence of an oxidant such as sodium hypochlorite, hydrogen peroxide or an alkyl hydroperoxide.

The product of formula X can also be obtained by oxidation of a product of formula VIII wherein R is hydrogen under the conditions described above, followed by the protection of the nitrogen atom of the lactam of formula XI

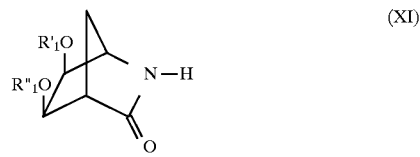 (XI)

wherein $R'_1$ and $R''_1$ are defined as above, by a protecting group as defined above.

The products of formula X and XI are particularly useful for the preparation of a carbo sugar of formula XII

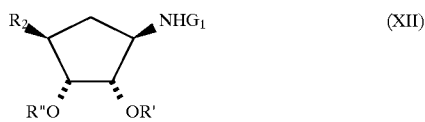 (XII)

wherein $R_2$ is carboxy, alkoxycarbonyl, N-alkylaminocarbonyl, hydroxymethyl or alkoxymethyl, and R' and R'' which may be identical or different, are hydrogen, acyl or aroyl, or $R'_1$ and $R''_1$ taken together with the carbon atom to which they are attached form an optionally substituted methylene group whose carbon atom is optionally substituted by one or two groups, which may be identical or different, selected from alkyl or phenyl, or two alkyl taken together can form cycloalkyl, and $G_1$ is hydrogen or a protecting group $G_2$ for the amino function. More particularly, $R_2$ is an ethylaminocarbonyl group or hydroxymethyl group, and R' and R'' together form an isopropylidene group.

The product of formula X can be transformed into a product of formula XII under conditions which are appropriate for the nature of the substituent $R_2$ which must be introduced.

The product of formula XII wherein $R_2$ is carboxy can be prepared by reacting a mineral base such as NaOH with the product of formula X, followed by the replacement of the protecting group $G_2$ by hydrogen and optionally groups $R'_1$ and $R''_1$ by hydrogen.

The product of formula XII, wherein $R_2$ is carboxy, can be obtained by the replacement of the protective group $G_2$ of formula X with a hydrogen atom, followed by the action of a mineral base such as sodium carbonate, and optionally replacing the radicals $R'_1$ and $R''_1$ by hydrogen.

The product of formula XII wherein $R_2$ is alkoxycarbonyl can be prepared by reacting an alkali metal alkoxide with the product of formula X, followed by the replacement of the protecting group $G_2$ by hydrogen and optionally of the groups $R'_1$ and $R''_1$ by hydrogen.

The product of formula XII, wherein $R_2$ is alkoxycarbonyl can be obtained by the replacement of the protective group $G_2$ of the product of formula X by hydrogen, followed by the action of an alkali metal alkoxide, and optionally replacing the radicals $R'_1$ and $R''_1$ by hydrogen.

The product of formula XII wherein $R_2$ is N-alkylaminocarbonyl can be prepared by reacting an alkylamine with the product of formula X, followed by the replacement of the protecting group $G_2$ by hydrogen and optionally of the groups $R'_1$ and $R''_1$ by hydrogen.

The product of formula XII, wherein $R_2$ is N-alkylaminocarbonyl, can be obtained by the replacement of the protective group $G_2$ of the product of formula X by hydrogen, followed by the action of an alkylamine, and optionally replacing the radicals $R'_1$ and $R''_1$ by hydrogen.

The product of formula XII wherein $R_2$ is a hydroxymethyl group can be prepared by reacting a reducing agent such as a borohydride, for example, sodium or potassium borohydride, with the product of formula X, followed by the replacement of the protecting group $G_2$ by hydrogen and optionally of the groups $R'_1$ and $R''_1$ by hydrogen.

The product of formula XII, wherein $R_2$ is a hydroxymethyl radical, can be obtained by replacement of protective group $G_2$ of the product of formula X by a hydrogen atom, followed by the action of a reducing agent such as sodium or potassium borohydride, and optionally replacing the radicals $R'_1$ and $R''_1$ by hydrogen.

The present invention also encompasses the isolation of the (1S) diastereomer of the compound of formula I' using optically-active organic acids of the opposite configuration to those described for isolating the (1R) diastereomer of the compound of formula I. According to the invention, the (1S) diastereomer of the compound of formula I' can then be converted the corresponding (1S) diastereomers of compounds of formulae IV, VI, VII, VIII, IX and X employing the methods used in preparing the (1R) diastereomeric compounds of those formulae.

The starting materials and intermediates are prepared by the application or adaptation of known methods.

The compounds of formulae XIII and XIII'

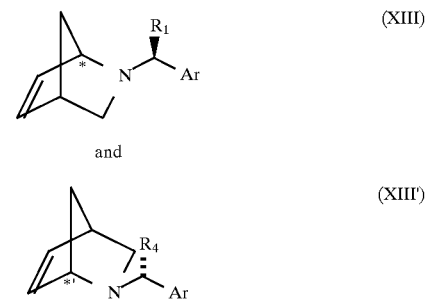

wherein *, *', $R_1$ and Ar are as previously defined, can be obtained by a Diels-Alder reaction between a mixture of homochiral amines of formulae

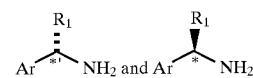

wherein *, *', $R_1$ and Ar are as previously defined, in the form of a salt, preferably with a mineral acid such as HCl, formaldehyde and cyclopentadiene working under the conditions described by S. D. Larsen and P. A. Grieco, J. Amer. Chem. Soc., Vol. 107, 1768–1769 (1985). This method leads to a mixture of two diastereoisomers. The diasteromers may be separated using L-dibenzoyl tartaric acid as described by C. K. -F. Chiu in Syn. Comm., 26(3), 577 (1996).

The compounds of formulae III and III' wherein R is hydrogen can be obtained by hydrogenolysis of the compounds of formula XIII and XIII' by means two step procedure. First the compounds are treated with 2,2,2-trichlorethoxycarbonyl (Troc) chloride or β-(trimethylsilyl) ethoxycarbonyl (Teoc) chloride to give the corresponding Troc or Teoc derivatives (carbamates) and treating with Zn in an alcoholic solvent such as ethanol with heating, or Zn in an organic acid solvent such as acetic acid at room temperature.

The present invention is further exemplified but not limited by the following illustrative examples which illustrate the preparation of the compounds according to the invention.

In the nuclear magnetic resonance (NMR) spectra the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXAMPLE 1a

Preparation of 2-(α-S-Methylbenzyl)-2-azabicyclo[2.2.1]hept-5-ene

In a 2 L reactor is charged 255 g of (S)-(–)-α-methylbenzylamine and 300 mL of water. The suspension is cooled to –5° C. and a solution of 185 mL of concentrated HCl in 100 mL of water is added with stirring over one hour. The pH of the mixture is adjusted to between 5 and 6.5. Stirring is continued for 30 minutes and then 242 mL of 37% formaldehyde solution is charged. After stirring for an additional 40 minutes, cyclopentadiene (~270 mL) is distilled directly into the reaction mixture. The resultant mixture is stirred vigorously overnight at –5° C. The completion of the reaction is determined by high-performance liquid chromatography (HPLC). The resulting two layers are separated and the aqueous layer is washed with 250 mL of heptane before basifying to a pH 11 with 168 mL of 50% NaOH solution and crushed ice. The organic mixture is then extracted with 2×500 mL and 2×300 mL portions of EtOAc. The combined extracts are washed with 200 mL of cold water, followed by 200 mL of saturated NaCl solution, dried over anhydrous $Na_2SO_4$ and filtered. The clear filtrate is concentrated by rotary evaporation to yield 408.4 g (97.4%) of a yellow oil, 2-(α-S-methylbenzyl)-2-azabicyclo[2.2.1]hept-5-ene, in a diastereomeric ratio of 77.1:22.9 in favor of the desired isomer.

$^1$H NMR (500 MHz, $CDCl_3$): δ 1.35 (d, 2H); 1.46 (d, 1H); 1.62 (d, 1H); 2.89 (d, 1H); 3.05 (m, 1H); 4.13 (s, 1H); 6.11 (d, 1H); 6.32 (m, 1H); 7.26 (d, 2H); 7.33 (d, 2H); MS (EI, 70eV) m/z (relative intensity): 199 (M+, 70)

EXAMPLE 1b

Preparation of 2-(α-S-Methylbenzyl)-2-azabicyclo[2.2.1]hept-5-ene

Into a 250-mL three-necked flask equipped with a cooling apparatus and stirring system, a solution is introduced under an argon atmosphere, which solution consists of 20 g of (S)-(–)-α-methylbenzylamine (165 mmol) in 60 mL of water whose pH is adjusted to 6.1 by the addition of 17 mL of 36% HCl (W/V). After cooling to 5° C., 20 mL of a 37% (W/V) aqueous formaldehyde solution are added. The solution is stirred for 5 minutes at 5° C.; then 21.8 g of cyclopentadiene (330 mmol) are added. The mixture is stirred for 16 hours between –5° and 0° C. The aqueous phase is separated by decanting and then washed with 50 mL of pentane. Neutralization to pH 8 is achieved by addition of concentrated NaOH. Two extractions are then carried out, each with 70 mL of EtOAc. The pH of the aqueous phase is adjusted to 11 by the addition of concentrated NaOH, followed by two extractions, each with 70 mL of EtOAc. The organic phases are combined, and then washed two times with 50 mL of water, and then they are dried over $Na_2SO_4$. After filtration and concentration to dryness at a reduced pressure, the yield consists of 33.1 g of 2-(α-S-methylbenzyl)-2-azabicyclo[2.2.1]hept-5-ene in the form of a slightly yellow oil.

EXAMPLE 2

Preparation of 5R,6S-Dihydroxy-2-(α-S-methylbenzyl)-2-azabicyclo[2.2.1]heptane

Into a 500-mL three-necked flask equipped with a cooling apparatus and a stirring system, containing a solution of 20 g of 2-(α-S-methylbenzyl)-2-azabicyclo[2.2.1]hept-5-ene (75.34 mmol) in 220 mL of t-butanol, 12 g of N-methylmorpholine oxide in 32 mL of water, at a temperature of approximately 25° C., are added, then 6.3 mL of a 25% (W/V) solution of osmium tetroxide ($OsO_4$) in t-butanol are added slowly. The stirring is continued for 2 hours at a temperature of approximately 20° C., then for 3 hours at 65° C. After evaporation of the t-butanol at a reduced pressure, the residue is redissolved in 350 mL of IPA. After concentration to dryness at a reduced pressure, 24 g of cis-5,6-dihydroxy-2-(α-S-methylbenzyl)-2-azabicyclo[2.2.1]heptane are produced in the form of an oil. 14 g of 5R,6S-dihydroxy-2-(α-S-methylbenzyl)-2-azabicyclo[2.2.1]heptane are produced by crystallization in cyclohexane, with an isomeric purity of more than 95%.

The NMR spectrum, determined in deuterochloroform, shows the following shifts (δ): 1.21 (3H, d); 1.38 (1H, d); 1.59 (1H, d); 2.22 (2H, m); 2.45 (1H, dd); 2.95 (1H, s); 3.99 (1H, q); 3.78 (1H, d); 3.90 (1H, d); 7.28 (5H, m).

EXAMPLE 3a

Preparation of 5R,6S-Dihydroxy-2-(α-S-methylbenzyl)-2-azabicyclo[2.2.1]heptane

A solution of 0.5 mmol of a mixture (78/22 in mol) of 5R,6S-dihydroxy-2-(α-S-methylbenzyl)-2-azabicyclo[2.2.1]heptane and 5S,6R-dihydroxy-2-(α-S-methylbenzyl)-2-azabicyclo[2.2.1]heptane and 0.5 mmol of L-dimethoxysuccinic acid in 1 mL of IPA is stirred for 24 hours at a temperature ranging from 25° C. at the beginning to 5° C. The crystals obtained are separated by filtration and dried. One thus obtains 110 mg of 5R,6S-dihydroxy-2-(α-S-methylbenzyl)-2-azabicyclo[2.2.1]heptane with an enantiomeric excess of 97%.

The mixture of 5R,6S-dihydroxy-2-(α-S-methylbenzyl)-2-azabicyclo[2.2.1]heptane and 5S,6R-dihydroxy-2-(α-S-methylbenzyl)-2-azabicyclo[2.2.1]heptane (78/22 in mol) may be obtained in the following manner:

In a 250 mL three-necked round-bottom flask provided with a coolant and a stirring system, containing a solution of 7 g 2-(α-S-methylbenzyl)-2-azabicyclo[2.2.1]hept-5-ene (35 mmol) in 70 mL of t-butanol, is added, at a temperature of approximately 25° C., 4.12 g of N-methylmorpholine oxide in 11 mL of water, then, 360 mL of a 2.5% solution (p/v) of osmium tetroxide ($OsO_4$) in t-butanol is slowly added. The mixture is stirred for 1 hour at a temperature of approximately 20° C., and then for 4 hours at 65° C. After the evaporation of the t-butanol under reduced pressure, the residue is taken up in 150 mL of IPA. After concentrating until dry under reduced pressure, one obtains 8.27 g of a product, the NMR spectrum of the proton of which shows that it is composed of a mixture (78/22 in mol) of 5R,6S-dihydroxy-2-(α-S-methyl-benzyl)-2-azabicyclo[2.2.1]heptane and 5S,6R-dihydroxy-2-(α-S-methyl-benzyl)-2-azabicyclo[2.2.1]heptane.

EXAMPLE 3b

Preparation of 5R,6S-Dihydroxy-2-(α-S-methylbenzyl)-2-azabicyclo[2.2.1]heptane

In a 50 mL one-necked round bottom flask provided with a magnetic stirrer and a coolant is charged 1 g of 2-(α-S-methylbenzyl)-2-azabicyclo[2.2.1]hept-5-ene (5 mmol), 2.5 mL of di-i-propyl ether, 2.5 mL of acetone, 0.9 mL of 58 w % aq. N-methylmorpholine oxide and 0.15 mL water. The mixture is stirred for 5 minutes and 9 mg of solid $K_2OsO_4 \cdot 2H_2O$ is charged in once and stirring is continued at room temperature for 25 minutes. The mixture is then stirred at reflux for 7.5 hours. HPLC shows after that time a 95% completion of the oxidation reaction. To the brown mixture cooled to room temperature is added a solution of 630 mg of sodium sulfite in 4 mL of water. The biphasic mixture is stirred at room temperature for 1 hour. Most of the organic solvents are evaporated under reduced pressure, 5 mL of di-i-propyl ether are added. The aqeous phase is separated by decantation and reextracted by 2×5 mL di-i-propyl ether. The combined organic phases are washed with an aqueous saturated sodium chloride solution, dried on $Na_2SO_4$, filtered and evaporated under reduced pressure to yield 1.04 g (89%, corrected yield=86%) of 5R,6S-dihydroxy2-(α-S-methylbenzyl)-2-azabicyclo[2.2.1]heptane as an oil that precipitates on standing. The product is 95% mol. pure by $^1H$ NMR in $CDCl_3$ (contain 4 mol. % N-methylmorpholine+0.6 mol. % starting material).

EXAMPLE 3c

Preparation of 5R,6S-Dihydroxy-2-(α-S-methylbenzyl)-2-azabicyclo[2.2.1]heptane L-tartrate To a 2 L reactor is charged 210 g of 2-(α-S-methylbenzyl)-2-azabicyclo[2.2.1]hept-5-ene, 1,200 mL of 2-methyl-2-propane and 182 mL of 4-methymorpholine N-oxide. To this mixture is charged, in dropwise fashion, 8 mL of a 2.5% solution of osmium tetroxide in t-butanol. Under nitrogen the mixture is heated to 62° C. with vigorous stirring for 22 hours. The reaction mixture is concentrated by rotary evaporation at 60° C. 300 mL of IPA is charged and the solution is again concentrated at 60° C. to yield 246 g of 5R,6S-Dihydroxy-2-(α-S-methylbenzyl)-2-azabicyclo-[2.2.1]heptane as a dark brown syrup. The crude product is suspended in 1.8 L of 75% IPA at 40° C. To the suspension is added 158.2 g of L-tartaric acid with vigorous stirring. Agitation is continued at 40° C. for 2.5 hours. The mixture is cooled to 30° C., filtered, washed with 500 mL of 75% IPA and 200 mL of IPA, then dried at 70° C. in vacuo for 16 hours to give 269.5 g of the desired L-tartrate salt as a cream colored solid (MP 143°–145° C., diastereomeric ratio of 94.2:5.8).

$^1H$ NMR (500 MHz, $CDCl_3$): δ 1.3 (d, 3H); 2.5 (m, 2H); 4.18 (s, 2H); 7.36 (t, 2H); 7.4 (t, 2H); MS (EI, 70eV) m/z (relative intensity): 233 (M+, 13)

EXAMPLE 4a

Preparation of 5R,6S-isopropylidenedioxy-2-(α-S-methylbenzyl)-2-azabicyclo[2.2.1]heptane Into 500-mL three-necked flask, equipped with a cooling apparatus and a stirring system, containing a solution of 18.4 g of 5R,6S-dihydroxy-2-(α-S-methylbenzyl)-2-azabicyclo[2.2.1]heptane (76 mmol) in 130 mL of toluene, 31.7 g of 2,2-dimethoxypropane (304 mmol) and then 13 g of TFA are added slowly (114 mmol). The mixture is heated for 4 hours 10 minutes at 65° C. After cooling to 30° C. and concentration in the rotary evaporator to eliminate the toluene, the excess 2,2-dimethoxypropane and partially the TFA, the reaction mixture is taken up in dichloromethane, then it is neutralized by the addition of 100 mL of 2N NaOH. After decanting, drying of the organic phase over $Na_2SO_4$, filtration, treatment with decolorizing charcoal (30 g) for 30 minutes at the boiling point of dichloromethane, filtration through Clarcel® and concentration to dryness at reduced pressure, the yield consists of 18.8 g of 5R,6S-isopropylidenedioxy-2-(α-S-methylbenzyl)-2-azabicyclo-[2.2.1]heptane, whose structure is confirmed by the proton NMR spectrum, which, determined in deuterochloroform, shows the following shifts (δ): 1.22 (3H, d); 1.23 (6H, s); 1.31 (1H, d); 1.57 (1H, d); 2.08 (1H, d); 2.34 (1H, broad s); 2.45 (1H, dd); 3.06 (1H, s); 3.40 (1H, q); 4.09 (1H, d); 4.19 (1H, d); 7.26 (5H, m).

EXAMPLE 4b

Preparation of 5R,6S-isopropylidenedioxy-2-(α-S-methylbenzyl)-2-azabicyclo[2.2.1]heptane To a 2-liter, 4-neck, jacketed cylindrical reactor equipped with a thermocouple, overhead stirrer and condenser is charged 223 g of 5R,6S-dihydroxy-2-(α-S-methylbenzyl)-2-azabicyclo[2.2.1]heptane L-tartrate followed by 1200 mL IPA. Agitation is begun and the flask charged 286 mL of 2,2-dimethoxypropane and 44.6 mL of TFA. The suspension is heated to 72° C. until all the solids dissolved. After 5 hours, the reaction is cooled to 65° C. and the contents transferred to a 3 L round bottom flask. Approximately 1100 mL of solvent is removed at 48° C. and 124 mbar vacuum. To the original 2-liter, 4-neck, jacketed cylindrical reactor is added 1.2 L of 2M NaOH with stirring at 25° C. To the NaOH solution, is charged the residue from the distillation described above (~700 mL of solution). The tan solution is cooled to 25° C. over 40 minutes. Solids begin to precipitate from the solution at 28° C. The suspension is stirred several hours before being filtered through an 11 cm Buchner funnel fitted with Whatman #1 filter paper. The filter cake is washed with 300 mL of water. The off-white solids are slurried in water for 13 hours and refiltered, washed with water and air dried. The solids are then vacuum dried at 50° C. to yield 112 g of 5R,6S-isopropylidenedioxy-2-(α-S-methylbenzyl)-2-azabicyclo[2.2.1]heptane as a white solid which according to HPLC is diastereomerically pure.

$^1H$ NMR (500 MHz, $CDCl_3$): δ 1.28 (s, 3H); 1.27 (d, 3H); 1.39 (s, 3H); 1.63 (d, 1H); 2.27 (d, 1H); 2.4 (d, 1H); 2.51 (dd, 1H); 3.12 (s, 1H); 3.46 (q, 1H); 4.2 (dd, 2H); 7.28 (m, 5H); MS (EI, 70eV) m/z (relative intensity): 273 (M+, 8.4)

EXAMPLE 5a

Preparation of 5R,6S-isopropylidenedioxy-2-(t-butoxycarbonyl)-2-azabicyclo[2.2.1]heptane In a 250-mL three-necked flask equipped with a stirring system are combined, 0.5 g of 5% palladium on charcoal, 5 g of 5R,6S-isopropylidenedioxy-2-(α-S-methylbenzyl)-2-azabicyclo[2.2.1]heptane, 3.98 g of di-t-butyl dicarbonate and 36 mL of methanol. The apparatus is purged with argon and then with hydrogen, and then it is placed under a hydrogen atmosphere at 25° C. The reaction is continued for 5 hours by carrying out a purge with hydrogen every 15 minutes to eliminate the carbon dioxide formed.

After filtration through Clarcel® and concentration to dryness at a reduced pressure, the yield consists of 4.84 g of 5R,6S-isopropylidenedioxy-2-(t-butoxycarbonyl)-2-azabicyclo[2.2.1]heptane, whose structure is confirmed by the NMR spectrum, which, determined in dimethyl sulfoxide-d6, shows the following chemical shifts (δ): 1.16 (s, 3H); 1.28 (s, 3H); 1.32 (s, 1H); 1.34 (s, 3H); 1.65 (d, 1H); 2.38 (m, 1H); 2.65 (d, 1H); 2.99 (m, 1H); 3.84 (m, 1H); 3.94 (d, 1H); 4.16 (d, 1H).

EXAMPLE 5b

Preparation of 5R,6S-isopropylidenedioxy-2-(t-butoxycarbonyl)-2-azabicyclo[2.2.1]heptane To a 2-liter, 4-neck, jacketed, cylindrical reactor equipped with a thermocouple, overhead stirrer, gas bladder and a septum for nitrogen and hydrogen inlet is charged in succession; 140 g of 5R,6S-isopropylidenedioxy-2-(α-S-methylbenzyl)-2-azabicyclo[2.2.1]heptane, 13.4 g of 10% Pd/C and 900 mL of methanol. The stirred suspension is sparged with nitrogen for 10 minutes followed by hydrogen for 10 minutes at 25° C. This procedure is repeated every 30 minutes and the reaction is monitored by TLC (silica gel, EtOAc, visualized with iodine). After 3 hours, the reaction is 50% complete according to TLC. To this partially reduced solution is charged 56 g of di-t-butyldicarboxylate over 10 minutes followed by a nitrogen/hydrogen sparge as described above. Every 30 minutes, an additional 10 g of di-t-butyldicarboxylate is added, followed by a nitrogen/hydrogen sparge until a total of 112 g of di-t-butyldicarboxylate is added (56 g plus 10 g charges). The reaction mixture is stirred overnight at 25° C. The Pd/C suspension is filtered through a 9 cm Buchner funnel fitted with #54 filter paper and a bed of 5 g of Celite and the reactor and filter cake are washed with 100 mL of methanol. The filtrate is placed in 2 liter 1-neck round bottom flask and 750 mL of solvent is removed at 40° C. and 105 mbar (~250 mL of a light yellow solution remained). To the original reaction vessel, is charged 1 L of water which is cooled to 10° C. The yellow residue from the above distillation is added to the cold water in virtually one portion. 5R,6S-Isopropylidenedioxy-2-(t-butoxycarbonyl)-2-azabicyclo[2.2.1]heptane precipitates from the solution as a white solid. The slurry is stirred for 30 minutes at 6° C. before filtering and washing with water. The resulting white solids are vacuum dried at 60° C. to yield 129.6 g of white solid which according to chiral HPLC is enantiomerically pure.

$^1$H NMR (500 MHz, CDCl$_3$): δ 1.28 (s, 3H); 1.4 (s, 3H); 1.45 (s, 9H); 1.87 (d, 1H); 2.53 (s, 1H); 2.82 (d, 1H); 3.17 (dd, 1H); 4.09 (m, 2H); 4.2 (m, 2H); MS (FAB-LRP) m/z (relative intensity): 270 ((M+H)+, 9.4)

EXAMPLE 6a

Preparation of 5R,6S-isopropylidenedioxy-2-(t-butoxycarbonyl)-2-azabicyclo[2.2.1]heptan-3-one In a 30-mL tube, 270 mg of 5R,6S-isopropylidenedioxy-2-(t-butoxycarbonyl)-2-azabicyclo[2.2.1]heptane (1 mmol) and 40 mg of RuO$_2$.H$_2$O (0.3 Eq) are introduced. 10 mL of EtOAc and 720 mg of water (40 Eq) are added. Then, 2.14 g of sodium periodate (10 Eq) are added, and the tube is sealed hermetically. The stirring is continued for 16 hours at 50° C. The reaction mixture is filtered through Clarcel®, and then two extractions are carried out, each with 20 mL of EtOAc. The organic phases are dried over Na$_2$SO$_4$. After the filtration and concentration to dryness at a reduced pressure, 245 mg of a solid are obtained, containing 68% of 5R,6S-isopropylidenedioxy-2-(t-butoxycarbonyl)-2-azabicyclo[2.2.1]heptan-3-one and 32% of starting material. The structure of the product obtained is confirmed by the NMR spectrum, which, determined in dimethyl sulfoxide d$_6$, shows the following chemical shifts (δ): 1.38 (9H, s); 1.23 (3H, s); 1.33 (3H, s); 1.85 (1H, d); 1.93 (1H, d); 2.69 (1H, s); 4.24 (1H, s); 4.41 (1H, d); 4.51 (1H, d).

EXAMPLE 6b

Preparation of 5R,6S-isopropylidenedioxy-2-(t-butoxycarbonyl)-2-azabicyclo[2.2.1]heptan-3-one To a 2 liter 4-neck jacketed cylindrical reactor equipped with a thermocouple, overhead stirrer, and condenser is charged in succession: 120 g of 5R,6S-isopropylidenedioxy-2-(t-butoxycarbonyl)-2-azabicyclo[2.2.1]heptane, 0.3 g of RuO$_2$, 201.2 g of sodium bromate, 960 mL of EtOAc, and 1000 mL of water with stirring. The reaction mixture is heated to 45° C. and stirred at this temperature for 15 hours. The stirring is discontinued and the aqueous layer discarded. Saturated NaCl (500 mL) is added to the reaction vessel and the suspension is stirred for 10 minutes. Stirring is again discontinued, the layers are allowed to separate and the aqueous layer removed. A 33% maleic acid disodium salt solution (500 mL) is charged to the reaction vessel, the suspension stirred for 5 minutes and the layers again separated. The organic layer is then filtered through a bed of Celite to remove the catalyst and the solvent is removed in vacuo. The resulting solid is dried in a vacuum oven to yield 117 g of 5R,6S-isopropylidenedioxy-2-(t-butoxycarbonyl)-2-azabicyclo[2.2.1]heptan-3-one as a white solid contaminated with 5% starting material. A 115 g sample of this material is dissolved in 350 mL of heptane at 85° C. and allowed to cool to 25° C. over about 3 hours then to 5° C. before filtration and drying in vacuo at 60° C. 92 g (74%) of 5R,6S-isopropylidenedioxy-2-(t-butoxycarbonyl)-2-azabicyclo-[2.2.1]heptan-3-one is obtained as a white crystalline solid.

$^1$H NMR: δ 1.32 (m, 3H); 1.48 (m, 12H); 1.82 (m, 1H); 2.1 (m, 1H); 4.43 (m, 1H); 4.48 (m, 1H); 4.6 (m, 1H); MS (FAB-LRP in nitrobenzyl alcohol): 284 ((M+H)+, 10%)

EXAMPLE 7a

Preparation of 2R,3S-isopropylidenedioxy-4R-amino-1S-ethylaminocarbonylcyclopentane benzoate In a Berghoff tube is placed 568 mg of 5R,6S-isopropylidenedioxy-2-(t-butoxycarbonyl)-2-azabicyclo[2.2.1]heptan-3-one and 10 mL of a 70% aqueous solution of ethylamine (by weight). The mixture is heated for 4 hours at 60° C. while stirring. After cooling, the excess ethylamine and water is eliminated under reduced pressure. After drying under reduced pressure, one thus obtains 98% yield of 650 mg of 2R,3S-isopropylidenedioxy-4-R-t-butoxycarbonylamino-1-S-ethylaminocarbonyl cyclopentane, the structure of which is confirmed by the NMR spectrum of the proton, and the rotatory power of which is $[α]^D_{20}$=15.0 (c=1; methanol).

To a solution of 200 mg of 2R,3S-isopropylidenedioxy-4R-t-butoxycarbonylamino-1-S-ethylaminocarbonyl cyclopentane in 1.6 mL of anhydrous dichloromethane is added 275 mL of TFA. The mixture is stirred overnight at a temperature of approximately –5° C. The reaction mixture is poured into 4 mL of 2.5N aqueous sodium carbonate. The organic layer is concentrated under reduced pressure at a temperature below 25° C. One thus obtains 125 mg of a product which is dissolved in 0.5 mL tetrahydrofuran. To this solution is added 70 mg of benzoic acid. After cooling the solution obtained to a temperature of approximately 0° C., the crystals obtained are separated by filtration and washed in pentane. One thus obtains 138 mg of 2R,3S-isopropylidenedioxy-4R-amino-1S-ethylaminocarbonyl cyclopentane benzoate.

EXAMPLE 7b

Preparation of 2R,3S-isopropylidenedioxy-4R-amino-1S-ethylaminocarbonylcyclopentane trifluoroacetate In a 25-mL autoclave, equipped with a magnetic stirrer, 1.47 g of 5R,6S-isopropylidenedioxy-2-(t-butoxycarbonyl)-

2-azabicyclo[2.2.1]heptan-3-one in a solution in 10 mL of anhydrous toluene is introduced, followed by approximately 0.7 mL of ethylamine. The autoclave is closed and then heated at a temperature between 90° and 100° C. for 21 hours. After cooling, the toluene is evaporated, and the dissolution is carried out with 10 mL of dichloromethane and 10 mL of water. After decanting, the organic phase is washed with 10 mL of water. The combined aqueous layers are washed in 10 mL of dichloromethane. The combined organic phases are washed with 10 mL of a saturated sodium chloride solution and then dried over $Na_2SO_4$. After filtration and concentration to dryness at a reduced pressure, the yield consists of 1.58 g of a product containing 95% 2R,3S-isopropylidene-dioxy-4R-t-butoxycarbonylamino-1-S-ethylaminocarbonylcyclopentane, whose structure is confirmed by the NMR spectrum, which, determined in dimethyl sulfoxide-d6, shows the following chemical shifts: 0.95 (t, 3H); 1.14 (s, 3H); 1.31 (s, 12H); 1.55 (m, 1H); 2.11 (m, 1H); 2.64 (m, 1H); 3.00 (q, 2H); 3.77 (m, 1H); 4.23 (m, 1H); 4.54 (m, 1H); 7.07 (d, 1H); 8.12 (t, 1H).

In a 25-mL flask, 1.22 g of 2R,3S-isopropylidenedioxy-4R-t-butoxycarbonylamino-1S-ethylaminocarbonylcyclopentane and 10 mL of dichloromethane are introduced. At a temperature of approximately 25° C., 0.85 g of TFA is added with stirring. After 6 hours of stirring and concentration to dryness, the yield consists of 1.16 g of 2R,3S-isopropylidenedioxy-4R-amino-1S-ethylaminocarbonylcyclopentane trifluoroacetate, whose structure is confirmed by the NMR spectrum, which, determined in dimethyl sulfoxide-d6, shows the following chemical shifts: 0.79 (t, 3H); 1.03 (s, 3H); 1.19 (s, 3H); 1.42 (m, 1H); 2.05 (m, 1H); 2.52 (m, 1H); 2.89 (q, 2H); 3.04 (m, 1H); 4.16 (m, 1H).

EXAMPLE 7c

Preparation of 2R,3S-isopropylidenedioxy-4R-amino-1S-ethylaminocarbonyl cyclopentane To a solution of 167 mg of 5R,6S-isopropylidenedioxy-2-(t-butoxycarbonyl)-2-azabicyclo[2.2.1]heptan-3-one in 1 mL of dichloromethane, cooled to 0° C., is added 90 μL of TFA. The temperature is allowed to rise to 23° C. over 40 minutes, then stirred for 22 hours at this temperature. Another 90 μL of TFA is added and then stirred for another one hour at a temperature of 23° C. After evaporating under reduced pressure, one obtains 123 mg of 5R,6S-isopropylidenedioxy-2-azabicyclo[2.2.1]heptan-3-one, the purity of which, determined by HPLC, is approximately 92%, and the structure of which is confirmed by the NMR spectrum of the proton.

A solution of 10 g of 5R,6S-isopropylidenedioxy-2-azabicyclo[2.2.1]heptan-3-one in 100 mL in a 70% aqueous solution of ethylamine (by weight) is heated to 110° C. for 20 hours under standard pressure. After cooling, the excess ethylamine is eliminated under reduced pressure, then washed with dichloromethane to eliminate the starting product that did not react. The aqueous layer is then concentrated and dried. One thus obtains 10.54 g of 2R,3S-isopropylidenedioxy-4R-amino-1S-ethylaminocarbonyl cyclopentane.

The present invention may be embodied in other specific forms without departing from the spirit or essential attributes thereof.

We claim:
1. A compound of formula

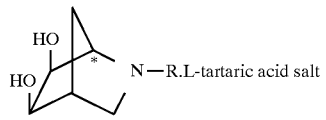

wherein

R is a group of formula

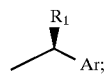

$R_1$ is alkyl; and

Ar represents a phenyl or α- or β-naphthyl group, optionally substituted by one or more atroms or groups, which are identical or different, selected from halogen atoms, alkyl groups having 1–4 carbon atoms, alkoxy groups having 1–4 carbon atoms or a nitro group.

* * * * *